US00PP27969P3

(12) United States Plant Patent
Davey et al.

(10) Patent No.: US PP27,969 P3
(45) Date of Patent: May 2, 2017

(54) ***HELLEBORUS* PLANT NAMED 'EPB 20'**

(50) Latin Name: *Helleborus×hybridus*
Varietal Denomination: EPB 20

(71) Applicants: Rodney Davey, Axminster (GB); Lynda Windsor, Axminster (GB)

(72) Inventors: Rodney Davey, Axminster (GB); Lynda Windsor, Axminster (GB)

( * ) Notice: Subject to any disclaimer, the term of this patent is extended or adjusted under 35 U.S.C. 154(b) by 6 days.

(21) Appl. No.: 14/756,539

(22) Filed: Sep. 15, 2015

(65) Prior Publication Data

US 2017/0079182 P1 Mar. 16, 2017

(51) Int. Cl.
*A01H 5/02* (2006.01)

(52) U.S. Cl.
USPC ..... Plt./439

(58) Field of Classification Search
USPC ..... Plt./439
See application file for complete search history.

*Primary Examiner* — Susan McCormick Ewoldt
(74) *Attorney, Agent, or Firm* — C. A. Whealy

(57) ABSTRACT

A new and distinct cultivar of *Helleborus* plant named 'EPB 20', characterized by its upright and mounding plant habit; uniform, continuous and freely flowering habit; relatively large greenish white-colored flowers that are held above the foliar plane on relatively long peduncles; and good garden performance.

2 Drawing Sheets

Botanical designation: *Helleborus×hybridus*.
Cultivar denomination: 'EPB 20'.

BACKGROUND OF THE INVENTION

The present invention relates to a new and distinct cultivar of *Helleborus* plant, botanically known as *Helleborus×hybridus* and hereinafter referred to by the name 'EPB 20'.

The new *Helleborus* plant is a product of a planned breeding program conducted by the Inventors in Devon, United Kingdom. The objective of the breeding program was to create new freely-flowering *Helleborus* plants with strong peduncles that hold numerous attractive flowers above the foliar plane.

The new *Helleborus* plant originated from a cross-pollination conducted by the Inventors in Devon, United Kingdom on Feb. 10, 2007 of a proprietary seedling selection of *Helleborus×hybridus* identified as code designation 1052XT, as the female, or seed, parent, not patented, with a proprietary seedling selection of *Helleborus×hybridus* identified as code designation 4861-LVP, as the male, or pollen, parent, not patented. The new *Helleborus* plant was discovered and selected by the Inventors as a single flowering plant from within the progeny of the stated cross-pollination grown in a controlled greenhouse environment in Devon, United Kingdom on Mar. 14, 2009.

Asexual reproduction of the new *Helleborus* plant by tissue culture in a controlled greenhouse environment in De Lier, The Netherlands since Oct. 10, 2012, has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype of the new *Helleborus* plant may vary somewhat with variations in environmental conditions such as temperature and light intensity without, however, any variance in genotype of the new *Helleborus* plant.

The following traits have been repeatedly observed and are determined to be the unique characteristics of 'EPB 20'. These characteristics in combination distinguish 'EPB 20' as a new and distinct *Helleborus* plant:

1. Upright and mounding plant habit.
2. Uniform, continuous and freely flowering habit.
3. Relatively large greenish white-colored flowers that are held above the foliar plane on relatively long peduncles.
4. Good garden performance.

Plants of the new *Helleborus* differ from plants of the female parent selection in the following characteristics:

1. Plants of the new *Helleborus* are shorter than plants of the female parent selection.
2. Plants of the new *Helleborus* and the female parent selection differ in flower color as plants of the female parent selection have white-colored flowers.

Plants of the new *Helleborus* differ from plants of the male parent selection in the following characteristics:

1. Plants of the new *Helleborus* are shorter than plants of the male parent selection.
2. Plants of the new *Helleborus* and the male parent selection differ in flower color as plants of the male parent selection have light purple-colored flowers.

Plants of the new *Helleborus* can be compared to plants of *Helleborus×hybridus* 'EPBRD01', disclosed in U.S. Plant Pat. No. 25,685. In side-by-side comparisons conducted in Devon, United Kingdom, plants of the new *Helleborus* differed from plants of 'EPBRD01' in the following characteristics:

1. Plants of the new *Helleborus* had longer leaves than plants of 'EPBRD01'.
2. Plants of the new *Helleborus* had larger inflorescences and were more freely flowering than plants of 'EPBRD01'.

3. Plants of the new *Helleborus* and 'EPBRD01' differed in flower bud color as plants of 'EPBRD01' had greenish white-colored flower buds.
4. Plants of the new *Helleborus* and 'EPBRD01' differed slightly in flower color as plants of 'EPBRD01' had light greenish white-colored flowers.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet is a side perspective view of a typical flowering plant of 'EPB 20' grown in a container.

The photograph on the second sheet is a close-up view of a typical flower bud and flowers of 'EPB 20'.

DETAILED BOTANICAL DESCRIPTION

The aforementioned photographs and following observations, measurements and values describe plants grown during the winter in three-liter containers in an outdoor nursery in Boijl, The Netherlands and under cultural practices typical of commercial *Helleborus* production. During the production of the plants, day temperatures ranged from 0° C. to 10° C. and night temperatures ranged from −15° C. to 0° C. Plants were one year old when the photographs and the description were taken. In the following description, color references are made to The Royal Horticultural Society Colour Chart, 2001 Edition, except where general terms of ordinary dictionary significance are used.

Botanical classification: *Helleborus hybridus* 'EPB 20'.

Parentage:

*Female, or seed, parent*.—Proprietary seedling selection of *Helleborus×hybridus* identified as code designation 1052XT, not patented.

*Male, or pollen, parent*.—Proprietary seedling selection of *Helleborus×hybridus* identified as code designation 4861-LVP, not patented.

Propagation:

*Type*.—By tissue culture.

*Time to initiate roots, summer*.—About 15 days at temperatures about 22° C. to 25° C.

*Time to produce a rooted young plant, summer*.—About two months at temperatures about 20° C.

*Root description*.—Fleshy, vigorous; typically white to brown in color, actual color of the roots is dependent on substrate composition, water quality, fertilizer type and formulation, substrate temperature and physiological age of roots.

Plant description:

*Plant and growth habit*.—Herbaceous perennial; upright and mounding plant habit with flowers held above the foliar plane; moderately vigorous to vigorous growth habit.

*Plant height*.—About 25 cm to 35 cm.

*Plant diameter* (*area of spread*).—About 20 cm to 25 cm.

*Stems*.—Strength: Strong. Aspect: Mostly upright. Texture: Smooth, glabrous. Luster: Shiny. Color: Close to 146C with spots, close to 187A.

Leaf description:

*Arrangement*.—Leaves arranged alternately in a basal rosette; leaves palmately compound with three to five leaflets per leaf.

*Leaflet length*.—About 12 cm to 15 cm.

*Leaflet width*.—About 8 cm to 10 cm.

*Leaflet shape*.—Ovate.

*Leaflet apex*.—Acute.

*Leaflet base*.—Acute.

*Leaflet margin*.—Serrate.

*Leaflet texture, upper and lower surfaces*.—Smooth, glabrous; leathery.

*Leaflet luster, upper surface*.—Shiny.

*Leaflet luster, lower surface*.—Somewhat shiny.

*Leaflet venation pattern*.—Pinnate.

*Leaflet color*.—Developing leaves, upper surface: Close to 137A; center, close to 193A. Developing leaves, lower surface: Close to 138B. Fully expanded leaves, upper surface: Close to 139A; venation, close to 139D, proximally, close to 187A. Fully expanded leaves, lower surface: Close to 137C; venation, close to 139C, proximally, close to 187A.

*Petioles*.—Length: About 10 cm to 16 cm. Diameter: About 5 mm to 7 mm. Texture, upper and lower surfaces: Smooth, glabrous. Color, developing leaves, upper and lower surfaces: Close to 146C; spots, close to 187A. Color, fully expanded leaves, upper and lower surfaces: Close to 146C; spots, close to N199A.

Flower description:

*Flower shape and habit*.—Single rotate flowers arranged in loosely branched cymes; freely flowering habit with typically about 15 to 20 flowers developing per cyme and up to 50 flowers developing per cyme in the second year of growth; flowers facing outwardly and somewhat drooping.

*Fragrance*.—None detected.

*Natural flowering season*.—Plants begin flowering about two months after planting; plants flower from January until March in the United Kingdom.

*Flower longevity on the plant*.—About two to three months; flowers persistent.

*Inflorescence height*.—About 25 cm to 30 cm.

*Inflorescence diameter*.—About 20 cm to 30 cm.

*Flower buds*.—Length: About 1 cm to 3 cm. Diameter: About 1 cm to 2 cm. Shape: Ovoid. Color: Close to 145C overlain with close to 186D.

*Flower diameter*.—About 8 cm.

*Flower depth* (*height*).—About 2 cm to 3 cm.

*Petals*.—None observed; transformed into nectaries.

*Sepals*.—Quantity and arrangement: Five arranged in a single whorl. Length: About 4 cm. Width: About 3 cm to 4 cm. Shape: Elliptic to obovate. Apex: Obtuse and occasionally emarginate. Base: Rounded. Margin: Mostly entire. Texture, upper and lower surfaces: Smooth, glabrous. Luster, upper and lower surfaces: Matte. Color: When opening and fully opened, upper surface: Close to 145D; color does not change with development. When opening and fully opened, lower surface: Close to 145D; towards the margins, close to 186D; color does not change with development.

*Peduncles*.—Length: About 20 cm. Diameter: About 5 mm to 10 mm. Strength: Strong. Aspect: Mostly upright. Texture: Smooth, glabrous. Color: Close to 146C; spots, close to 187A.

*Pedicels*.—Length: About 4 cm to 10 cm. Diameter: About 3 mm to 4 mm. Aspect: About 10° from peduncle axis. Strength: Strong. Texture: Smooth, glabrous. Color: Close to 146C; spots, close to 187A.

*Reproductive organs*.—Stamens: Quantity per flower: About 60. Filament length: About 1.5 cm to 1.8 cm. Filament color: Close to 157D. Anther shape: Elliptic to ovate. Anther length: About 2 mm. Anther color: Close to 10B. Pollen amount: Scarce. Pollen color: Close to 10B. Pistils: Quantity per flower: About five. Pistil length: About 2.5 cm. Stigma shape: Club-shaped. Stigma color: Close to 157C. Style length: About 1.5 cm. Style color: Close to 186D. Ovary color: Close to 142B.

*Nectaries*.—Quantity per flower: About 10 to 15. Length: About 5 mm to 8 mm. Width: About 3 mm. Shape: Funnelform. Color: Close to N144C; distally, close to 150B.

*Seeds and fruits*.—Seed and fruit development have not been observed on plants of the new *Helleborus*.

Garden performance: Plants of the new *Helleborus* have been observed to have good garden performance and to tolerate rain, wind and temperatures ranging from about −20° C. to about 35° C.

Pathogen & pest resistance: Plants of the new *Helleborus* have not been observed to be resistant to pathogens and pests common to *Helleborus* plants.

It is claimed:

1. A new and distinct *Helleborus* plant named 'EPB 20' as illustrated and described.

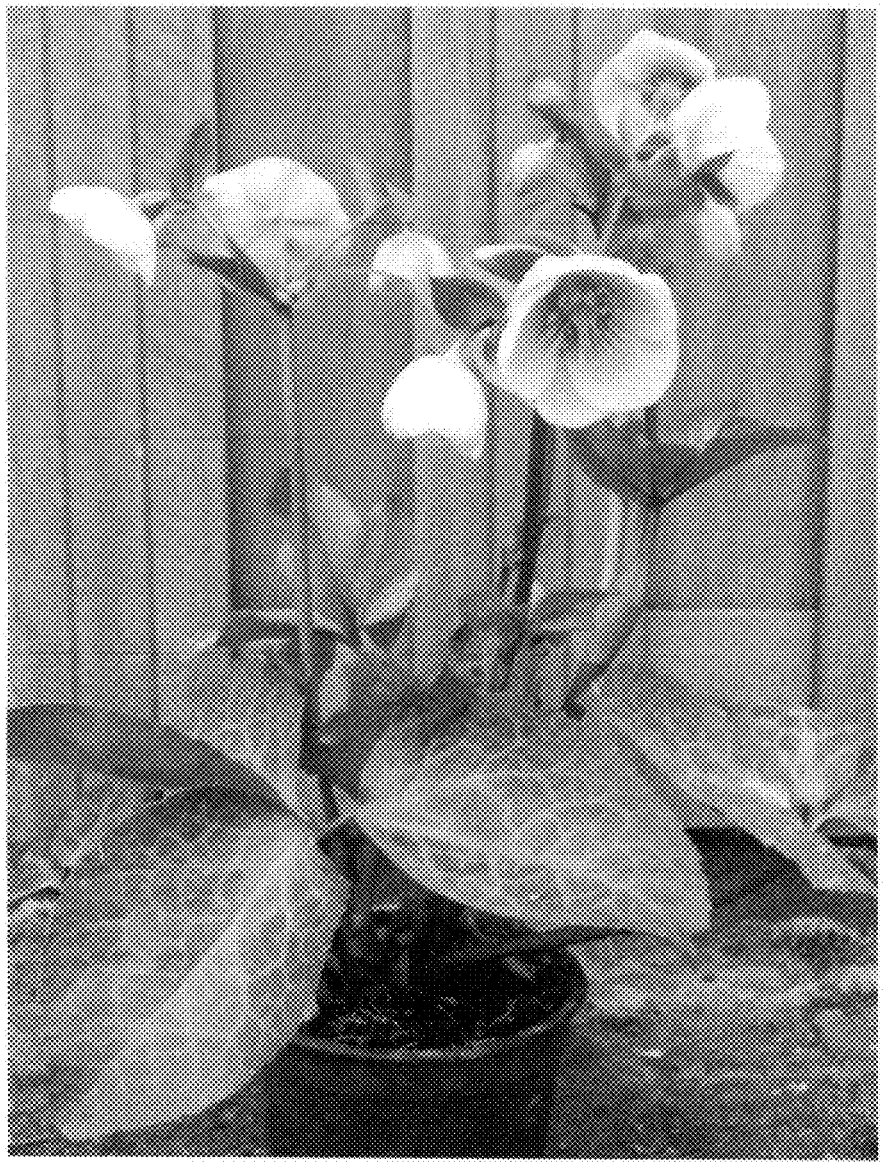

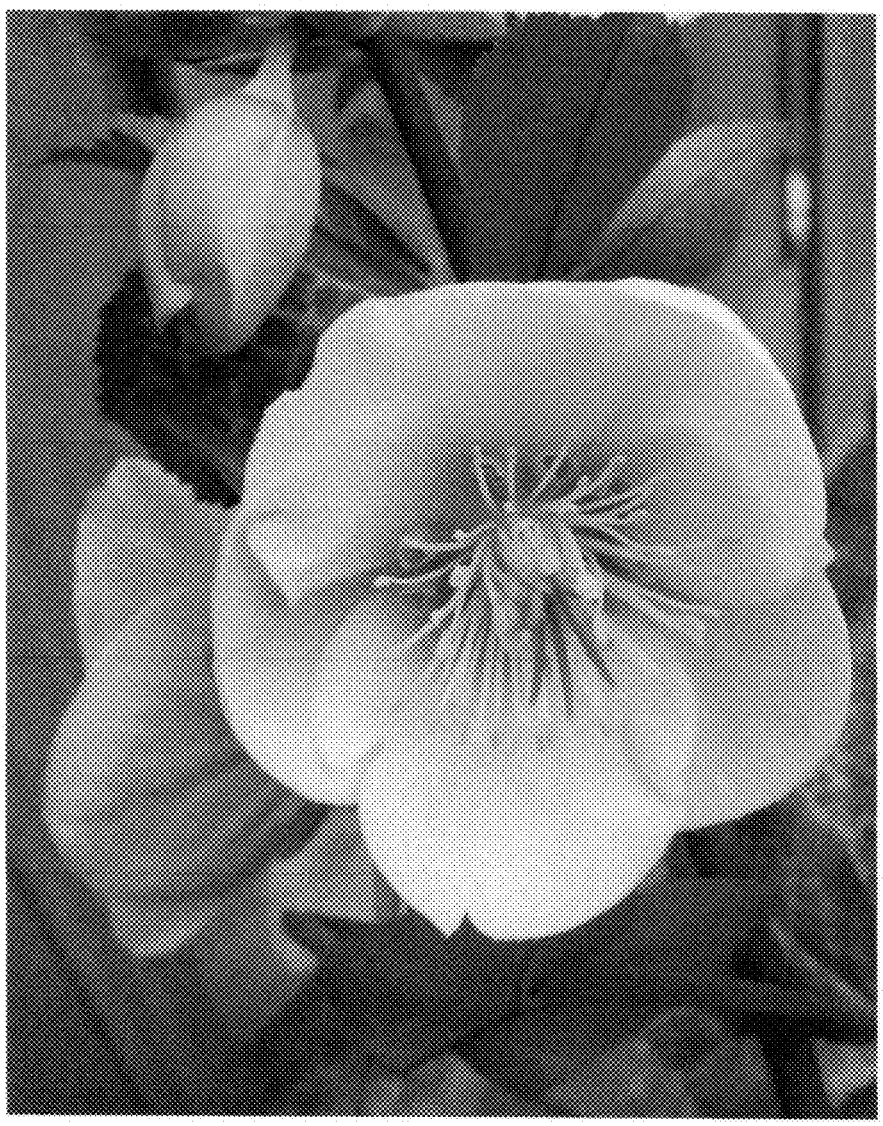

* * * * *